(12) United States Patent
Garonzik

(10) Patent No.: US 6,530,953 B2
(45) Date of Patent: Mar. 11, 2003

(54) METHOD OF MAGNETICALLY COUPLING A PROSTHESIS WITH AN OCULAR IMPLANT

(76) Inventor: Scott N. Garonzik, 4445 Woodfield Blvd., Boca Raton, FL (US) 33434

( * ) Notice: Subject to any disclaimer, the term of this patent is extended or adjusted under 35 U.S.C. 154(b) by 0 days.

(21) Appl. No.: 09/863,995

(22) Filed: May 23, 2001

(65) Prior Publication Data

US 2001/0047205 A1 Nov. 29, 2001

Related U.S. Application Data

(60) Provisional application No. 60/207,011, filed on May 25, 2000.

(51) Int. Cl.$^7$ ................................................. A61F 2/14
(52) U.S. Cl. ....................................................... 623/4.1
(58) Field of Search ................................ 623/4.1, 6.38, 623/6.39, 6.4, 6.41–5, 6.64

(56) References Cited

U.S. PATENT DOCUMENTS

| | | | | |
|---|---|---|---|---|
| 2,637,043 A | * | 5/1953 | Morrell ...................... | 335/302 |
| 5,192,315 A | * | 3/1993 | Jacob-LaBarre ........... | 623/6.64 |
| 6,099,564 A | * | 8/2000 | Perry ........................ | 623/11.11 |
| 6,187,041 B1 | * | 2/2001 | Garonzik .................... | 623/4.1 |

* cited by examiner

Primary Examiner—David J. Isabella
Assistant Examiner—Hieu Phan
(74) Attorney, Agent, or Firm—Robert M. Downey, P.A.

(57) ABSTRACT

An ocular replacement system provides a ball implant having an outer spherical surface that is receptive to ocular tissue ingrowth, including an anterior surface positioned forwardly within the eye cavity to create a semi-spherical shape covered by the conjunctiva. A prosthesis includes an inner concave surface shaped to conform generally to the anterior surface and to the conjunctiva covering the anterior surface of the implant. One or more first magnets or magnetically attractive elements fitted to and flush with the anterior surface of the implant are correspondingly positioned relative to one or more second magnets fitted to the inner concave surface of the prosthesis. In one embodiment, the poles of the first magnets are arranged to magnetically align with opposite poles of the second magnets, thereby providing an attractive force which magnetically couples the prosthesis to the implant. In another embodiment, the poles of the first magnets are arranged to align with like poles of the second magnets so that a repelling force exists between the second magnets on the prosthesis and the first magnets on the implant. The attracting or repelling forces between the first and second magnets allows the prosthesis to follow movement of the implant in a manner which simulates natural eye movement.

11 Claims, 3 Drawing Sheets

METHOD OF MAGNETICALLY COUPLING A PROSTHESIS WITH AN OCULAR IMPLANT

This application is based on provisional patent application Ser. No. 60/207,011 filed on May 25, 2000.

BACKGROUND OF THE INVENTION

1. Field of the Invention

This invention relates generally to a prosthetic eye, and, more particularly to an improved ocular replacement apparatus that provides for magnetic coupling of a prosthesis to an implant without the use of a post or other protruding structure, and allowing the conjunctiva tissue to be closed, thereby reducing the likelihood of irritation, infection and/or rejection of the implant.

2. Description of the Related Art

There are instances where an eye has become damaged due to trauma or disease wherein it is necessary to remove the entire eyeball from the eye cavity. Thereafter, a prosthetic eye may be replaced in the eye cavity to provide a cosmetically acceptable appearance, to reduce the psychological trauma associated with loss of an eye and to correct any medical problems associated with the loss of an eye.

Presently, the most accepted medical procedures for the removal of a diseased natural eye is to perform either an enucleation or an evisceration. Generally, enucleation involves first sedating the patient and anesthetizing the eye. The attaching ocular muscles and tissues are then dissected completely away from the patient's diseased natural eyeball. The conjunctiva and Tenon's capsule are incised down to the sclera as close as possible to the cornea. The extra ocular muscles are disinserted at the point of their insertion on the sclera. The optic nerve is severed and the natural eyeball is removed. While controlling bleeding, a porous plastic or coral ball-shaped implant is inserted into the eye cavity. Thereafter, the ocular muscles are sutured to the exterior, porous surface of the implant, or a homologous or autologous material wrap, in accordance with their correct anatomical positions. Once muscle attachment is completed, the Tenon's capsule and conjunctiva are closed up over the implant.

There are some instances where it is desirous to perform an evisceration rather than an enucleation of the eye. Evisceration can be performed for treatment of a blind painful eye if a rapid, less traumatic surgery, as compared to enucleation. In particular, evisceration may be desirable for old or very ill patients in whom general anesthesia is a risk. Generally, evisceration involves undermining the conjunctiva with scissors that the sclera around the limbus is free of conjunctiva. A keratome entry through the limbus into the anterior chamber of the eye is performed and curved corneal scissors is used to excise the entire cornea. An evisceration spoon is used to remove the intraocular contents while the globe is fixed by holding onto the limbal sclera with toothed forceps. Thereafter, the scleral shell is opened with forceps and the uveal tissue is scraped from inside the eye using a gauze square held in a hemostat. Bleeding is controlled by cautery. The implant can then be inserted within the cavity and, thereafter, the scleral shell is closed. The ocular muscles remain in tact and, in most cases, the patient has full mobility of the ocular globe.

In either an enucleation or an evisceration, the patient is measured for a cosmetic prosthesis after a healing period of approximately two months. After another four to six months, the prosthesis is integrated with the implant. At present, the most common method to fully integrate the prosthesis with the implant involves the use of a coupling post. To fit the post to the implant, the conjunctiva is incised and pulled partially apart to expose an anterior portion of the implant. A hole is then drilled approximately 5–7 mm deep into the implant, perpendicular to the anterior surface. The coupling post is then inserted and anchored within the hole so that an exposed end portion of the post protrudes approximately 2 mm beyond the conjunctiva. The conjunctiva is then pulled closed around the base of the post over the anterior surface of the implant. A hole or other means on the inner surface of the prosthesis receives the protruding end of the post so that the prosthesis remains attached to the post. Hence, as the muscles of the eye move the implant, the coupling post serves to move the prosthesis with the implant to simulate natural eye movement.

While the above-described procedure is the most effective method presently known to couple a prosthesis to an eye implant, patients have experienced numerous problems with this technique. Specifically, fully integrated prosthetic implant devices have been disappointing in the past because of associated complications, such as extrusion of the implant and conjunctival erosion. In some instances, movement of the prosthesis and coupling post relative to the conjunctiva has caused extreme irritation to the conjunctiva tissue, resulting in infection and rejection of the implant.

Various ocular replacement systems using magnetic coupling between the implant and prosthesis have been proposed in the related art. Examples of such systems are found in the U.S. patents to Jacob-LaBarre, U.S. Pat. No. 5,192,315 and Morrell, U.S. Pat. No. 2,637,043. In these ocular replacement systems, the implant includes a protruding structure (e.g., a post) which extends outwardly through the conjunctiva. A magnet is fitted to the end of the protruding structure for direct, mating attachment with a corresponding magnet fitted to the rear side of the prosthesis. As mentioned above, movement of the protruding structure relative to the conjunctiva causes irritation to the tissue. Furthermore, the open conjunctiva permits entry of bacteria and other microorganisms into the eye cavity which can lead to infection and rejection of the implant.

Accordingly, there is an urgent need in the related field for an improved ocular replacement system and method to more effectively couple a prosthesis to an eye implant so that the likelihood of irritation, infection and/or rejection of the implant is minimized and the need of a second surgical procedure is eliminated. Moreover, there is an urgent need for an ocular replacement system and method which allows for prosthetic eye movement using a magnetic coupling system, wherein the magnetic attraction is through the conjunctiva tissue, without disrupting the conjunctiva, thereby enabling the conjunctiva to be fully closed in a manner which prevents irritation and possible infection.

SUMMARY OF THE INVENTION

Generally, in accordance with the present invention, an apparatus for use in replacing the natural eye of a patient in an eye cavity is provided. More specifically, the present invention provides an ocular replacement system including a ball-shaped implant body sized and configured for receipt within the eye cavity and having an anterior surface positioned forwardly within the eye cavity to create a semi-spherical shape which is covered by the conjunctiva, and a prosthesis having an inner concave surface shaped to conform generally to the anterior surface of the implant and the covering conjunctiva.

In accordance with the system and method of the present invention, an improved means of coupling the prosthesis to the implant is provided, wherein one or more magnets are fitted to the rear concave side of the prosthesis for alignment with correspondingly positioned magnets or magnetically attractive elements fitted to the anterior surface of the implant. More particularly, magnets are fitted to both the prosthesis and the implant so that only a face of the magnets is exposed. The face of the magnets on both the prosthesis and the implant is either of a positive (+) or negative (−) magnetic pole. In one embodiment, the magnetic poles of the exposed magnet faces on the prosthesis are opposite to the magnetic poles of the exposed faces of the magnets on the implant, so that an attractive force exists between the first magnets on the implant and the correspondingly positioned second magnets on the prosthesis. In another embodiment, the poles of the exposed faces of the magnets on the prosthesis are the same as the poles of the exposed faces of the magnets on the implant so that a repelling force exists between the second magnets on the prosthesis and the first magnets on the implant. In either embodiment, as the implant moves, the magnetic attracting or repelling forces between the first magnets and the second magnets causes the prosthesis to follow movement of the implant in a manner which simulates natural eye movement.

Accordingly, it is an object of the present invention to provide an improved ocular replacement system and method of coupling a prosthesis to an implant.

More specifically, it is an object of the present invention to provide an ocular replacement system having an improved means for magnetically coupling of a prosthesis to an eye implant without damaging and/or irritating the ocular tissue.

It is yet another object of the present invention to provide an ocular replacement system which eliminates the need for a coupling post, thereby avoiding follow-up surgery after implant surgery.

It is a further object of the present invention to provide an improved ocular replacement system and method eliminating the need for traumatic surgical procedures to cut the conjunctiva and drill into the implant to fit a coupling post to the implant.

It is still another object of the present invention to provide an improved ocular replacement system and method which significantly reduces the likelihood of tissue irritation, infection and/or rejection of the implant.

These and other objects and advantages of the present invention will be more readily apparent with reference to the following detailed description and the accompanying drawings.

BRIEF DESCRIPTION OF THE DRAWINGS

For a fuller understanding of the nature of the present invention, reference should be made to the following detailed description taken in connection with the accompanying drawings in which.

Like reference numerals refer to like parts throughout the several views of the drawings.

DETAILED DESCRIPTION OF THE PREFERRED EMBODIMENTS

Figure 1:
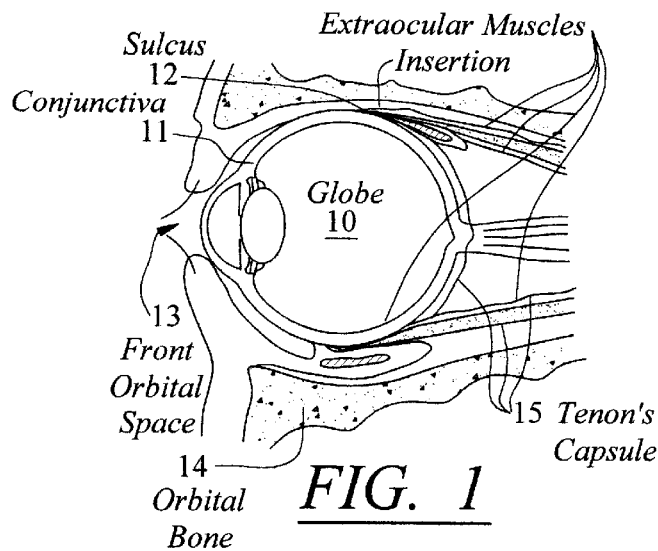
FIG. 1 is a side sectional anatomical view of a patient's eye, illustrating the orbit and its contents prior to surgery.

Referring initially to FIG. 1, a side sectional anatomical view of a patient's eye is shown to include an ocular globe (natural eyeball) 1 0, conjunctiva 11, sulcus 12, front orbital space 13, orbital bone 14, and Tenon's capsule 15. Hence, FIG. 1 illustrates the orbit and its contents prior to surgery.

Figure 2:
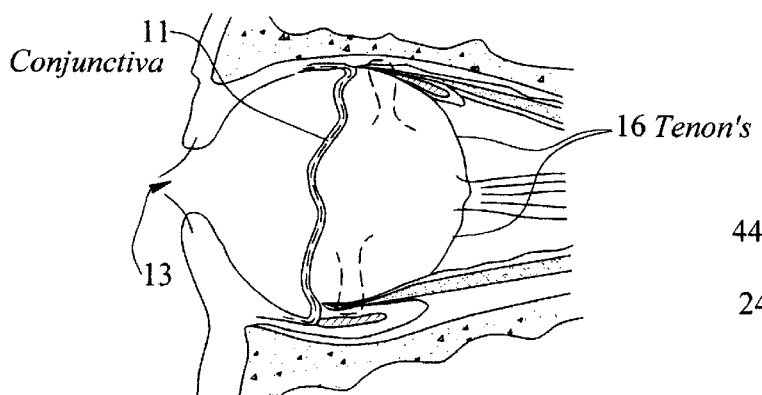
FIG. 2 is a side sectional anatomical view of a patient's eye, illustrating the orbit after enucleation.
Figure 5:
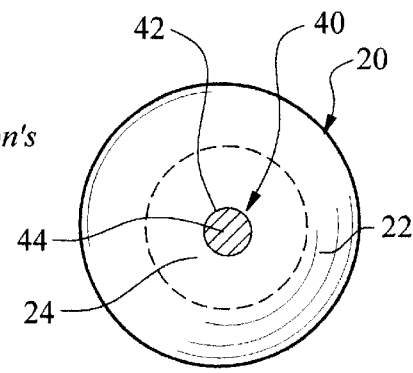
FIG. 5 is a front elevational view of the implant showing a magnet or attracting metal element embedded within the implant body so that the metal element is flush with the anterior surface of the implant, in accordance with one preferred embodiment of the magnetic coupling means.

If trauma or disease requires removal of the ocular globe 10, then an enucleation is generally performed. FIG. 2 illustrates the orbit after enucleation, showing the conjunctiva 11 and Tenon's 16 after the ocular glove 10 has been removed.

Figure 3:
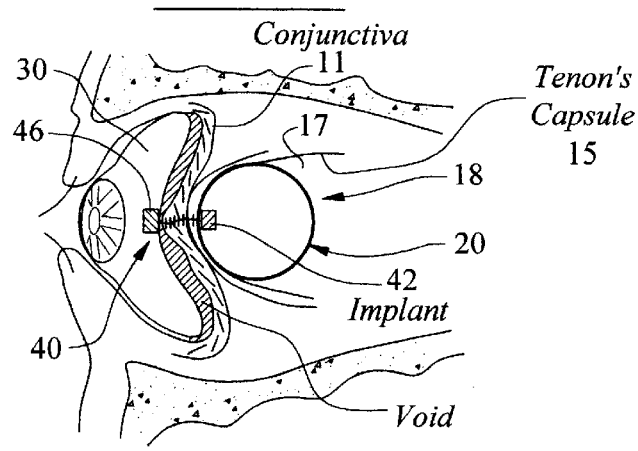
FIG. 3 is a side sectional anatomical view of the patient's eye, illustrating the eye implant and prosthesis of the replacement system of the present invention operatively received within the orbit.
Figure 6:
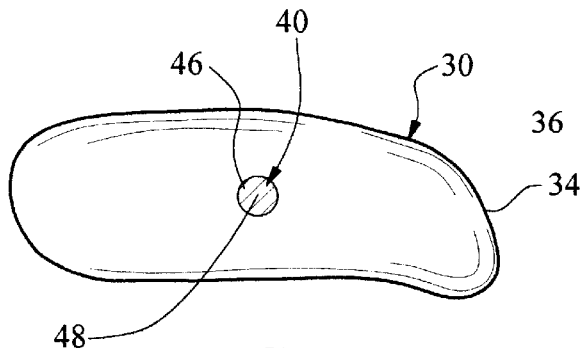
FIG. 6 is a rear elevational view of the prosthesis showing a magnet embedded within the concave surface thereof for magnetic alignment with the magnet of FIG. 5, in accordance with the one preferred embodiment of the magnetic coupling means.
Figure 9:
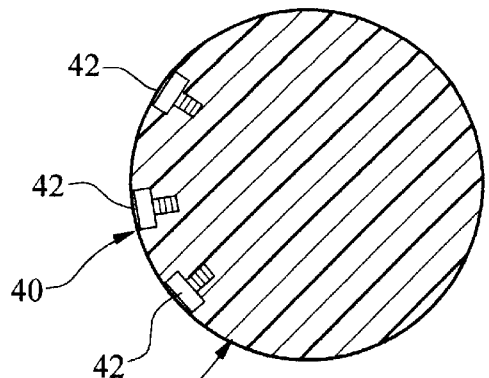
FIG. 9 is a sectional view of the implant showing a plurality of magnets or magnetically attractive metal elements fitted to the anterior portion so that the exposed face of each of the magnets is flush with the anterior surface of the implant.

Referring to FIG. 3, the ocular replacement apparatus 18 of the present invention is shown in accordance with an exemplary embodiment. The ocular replacement apparatus includes a generally ball-shaped implant body 20 which is sized and configured for receipt within the eye cavity 17 so that the implant body 20 substantially fills the eye cavity 17 surrounded by Tenon's capsule 15. The implant body 20 includes a generally spherical outer surface 22. It is preferred that the outer surface 22 be of a material and texture which is receptive to ingrowth of ocular tissue, including muscle tissue, so that the implant body 20 integrates with the tissue of the orbit. A coral implant body or plastic implant ball having a porous exterior spherical surface 22 are generally preferred. The outer surface 22 includes an anterior surface area 24 which is positioned forwardly in the eye cavity so that it mates with Tenon's capsule 15 while exerting minimal outward pressure to impart a generally spherical outer configuration to the conjunctiva.

The apparatus 18 further includes a prosthesis 30 formed of ceramic, glass, plastic or other suitable material. The prosthesis 30 includes an outer convex surface 32 which is provided with a cosmetically acceptable appearance to resemble the natural eye. The prosthesis 30 further includes a surrounding peripheral edge 34 which is shaped and configured to generally conform with the periphery of the conjunctiva. The peripheral edge 34 is generally rounded to provide a smooth surface, thereby preventing excessive irritation of the ocular tissue upon movement of the prosthesis. An inner concave surface 36 of the prosthesis is shaped to conform generally to the anterior surface area and the conjunctiva.

Magnetic coupling means 40 provide an attractive force between the anterior surface area 24 of the implant body 20 and the inner concave surface 36 of the prosthesis 30 to magnetically couple the prosthesis to the implant body. In this manner, the prosthesis follows movement of the implant body within the eye cavity without the need of connecting structure extending between the implant body and prosthesis and through the conjunctiva.

Figure 4:
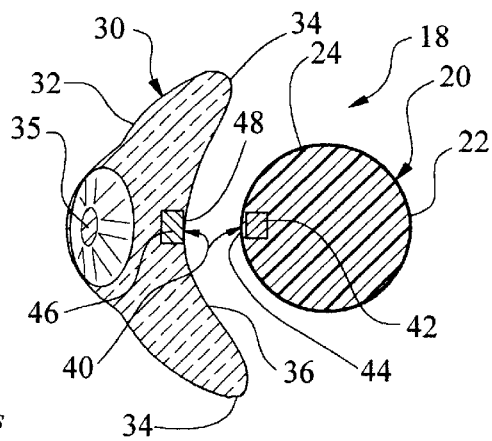
FIG. 4 is an isolated, sectional view of the implant and prosthesis of the present invention, in accordance with one preferred embodiment thereof, illustrating a magnet fitted to the concave side of the prosthesis for alignment with a correspondingly positioned magnet or magnetically attractive element fitted to the implant.

In one exemplary embodiment, as seen in FIG. 4, the magnetic coupling means includes a first element 42 which may be a magnet or a non-magnet formed of a magnetically attractive metal. The first element 42 is embedded with the anterior surface area 24 of the implant body so that an exposed face 44 is flush with the outer surface 22 of the implant body. A magnet 46 defining a second element is embedded within the concave surface 36 of the prosthesis so that an exposed face 48 of the magnet 46 is flush with the concave surface 36. The magnet 46 is specifically positioned on the inner concave surface 36 of the prosthesis so that the face 48 magnetically aligns with the face 44 of the first element 42. Determining the location of the magnet 46 on an inner concave surface 36 may be done during fitting of the prosthesis to the patient. Upon aligning the artificial eye 35 on the outer surface 32 of the prosthesis with the gaze position of the patient's natural eye, the position of the magnet 46 on the concave side of the prosthesis can be marked for magnetic alignment with the first element 42. Instrumentation may be necessary to identify the specific location of the first element 42 behind the conjunctiva. Once the position for the magnet 46 is determined, the inner concave surface 35 can be drilled to accept the magnet 46 therein so that the face 48 is flush with the concave surface.

The second magnet(s) 46 on the prosthesis do not actually make direct contact with the magnet(s) or magnet attracting element(s) 42 on the implant. Instead, a magnetic coupling between the magnet(s) 42 and magnet(s) 46 is provided through the tissue which covers the implant. Instead of using a magnet in the implant, a magnet attracting metal element may be chosen to avoid future surgery and replacement of magnets in the implant in the event it is discovered that the magnet(s) 42 looses power after a period of time. In this case, a magnet(s) 46 is used in the prosthesis only, thereby allowing for easy replacement when needed. This further facilitates adjusting the fit of the prosthesis and magnet position thereon, without disrupting the implant.

In each of the described embodiments, the faces 44 of the magnet(s) 42 or magnet attracting element(s) are flush with the outer circumferential surface of the implant. Further, it is preferable that the implant be of a material and design which promotes tissue regrowth and attachment to the implant. This is particularly important to maintain proper positioning of the implant within the socket, and to keep the implant from extruding or being rejected by the body. Additionally, the implant allows tissue growth around the magnet(s) or metal element(s) 42 which helps to keep the magnet(s) 42 in place. In the event a medical grade metal is used, the element 42 may be provided with a plastic (e.g., poly methyl methacrylite) or a polymer wash, in order to protect the elements 42 from deterioration.

Once the implant is placed in the eye cavity, the same muscles which were attached to the natural eye become attached to the implant, thereby allowing the implant to move in a natural manner. Normally, the person fitting the artificial eye to the patient will take an impression of the patient's eye socket to get the exact curvature of the socket so that the rear concave side of the prosthesis can match the curvature of the patient's eye socket (with the implant inserted). The magnet is fitted to the rear concave side of the prosthesis in position for alignment with the metal element 42 in the implant, without disrupting the conjunctiva. This is unlike any past magnetic ocular coupling system. In the past, the implant and artificial eye (i.e., prosthesis) were directly attached via structure which extends through the conjunctiva. This has caused an unacceptable rate of infection and failure. The present invention overcomes this problem by providing a magnetic coupling through the eye tissue, with no direct contact between elements 42 on the implant and elements 46 on the prosthesis and without disturbing the conjunctiva tissue covering the implant.

Figure 7:
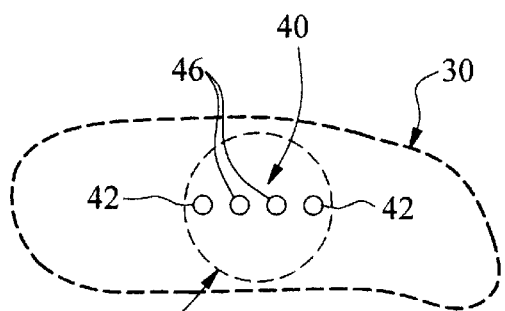
FIG. 7 is a diagrammatic view illustrating an arrangement of magnets on the prosthesis and correspondingly positioned magnets fitted to the implant in accordance with an alternative embodiment of the magnetic coupling means.
Figure 10:
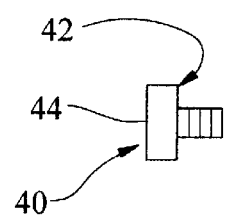
FIG. 10 is a side elevational view of the magnet or magnetically attractive element in accordance with the embodiment of FIG. 9.
Figure 8:
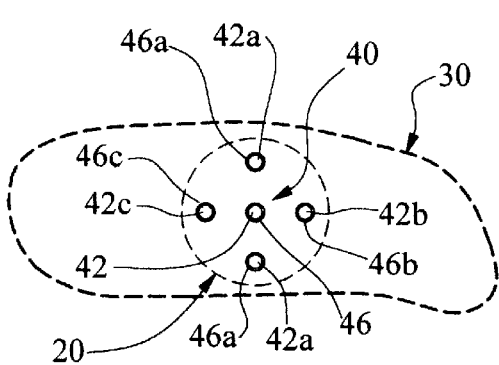
FIG. 8 is a diagrammatic view illustrating an arrangement of magnets on the prosthesis and correspondingly positioned magnets or magnetic attracting metal elements on the implant in accordance with yet another embodiment of the magnetic coupling means.

FIGS. 7 and 8 illustrate other exemplary embodiments of the present invention wherein the anterior surface area of the implant body is fitted with a plurality of first magnets or magnet attracting elements 42 and the prosthesis is fitted with a plurality of correspondingly aligned second magnets 46. Specifically, an arrangement of the first magnets 42 is provided on the anterior surface area in accordance with a desired, spaced array. The heads, including the face 44, of the first magnets 42 are sized and positioned to magnetically align with the exposed faces of the second magnets 46 on the prosthesis. The individual magnets 46 on the prosthesis are specifically positioned to fall into magnetic alignment with the corresponding individual magnets or magnetically attractive elements 42 on the implant body. Magnetic alignment of the respective magnets 46 and magnets 42 serves to create an attractive force, thereby magnetically coupling the prosthesis to the implant body. It should be noted that magnetic alignment of magnets 46 with magnets 42 does not necessarily require axial alignment. Rather, magnetic alignment, as used herein, refers to the existence of an attractive or repelling force between the magnets 46 and the corresponding magnets 42.

To promote up and down movement, a head having a size of approximately 2 to 3 mm can be placed on the prosthesis centrally but superior to a centrally placed, but inferior magnet head on the surface of the implant. To further enhance up and down movement of the prosthesis, as well as lateral movement of the prosthesis, the magnets 42 and 46 may be arranged as shown in FIG. 8. In this embodiment, upper and lower magnets 42a and 46a are arranged above and below the corresponding central magnets 42 and 46 on the implant and prosthesis, respectively. In use, the magnetic draw between the magnets 42a and the magnets 46a promotes upward movement of the prosthesis when the patient looks up and downward movement of the prosthesis when the patient looks down. To keep the prosthesis in place and to promote movement to the medial side, a magnet 46b is placed in the medial side of the prosthesis to align with a magnet 42b placed in the corresponding position on the implant. To promote movement to the lateral excursion, a magnet 46c is placed in the lateral side of the prosthesis to create a magnetic attraction with a correspondingly positioned magnet 42c on the implant. The heads of the magnets and metal elements may be of any size and shape which promotes a magnetic draw between the prosthesis and the implant, with the conjunctiva positioned therebetween.

Referring to FIG. 7, an alternative embodiment of the invention places the magnets 42 on the implant outboard relative to the magnets 46 on the prosthesis so that the magnets 42 are not directly aligned with the magnets 46. In this particular embodiment, the exposed faces of the magnets on both the prosthesis and the implant are of the same magnetic pole so that a repelling force exists between the magnets 42 and the magnets 46. In this instance, when the patient looks to the left or to the right, causing corresponding movement of the implant, the magnets 42 move in relation to the magnets 46 on the prosthesis. The repelling force between the magnets 42 and the magnets 46 causes the magnets 46 to avoid alignment with the magnets 42 resulting in the magnets 46 remaining inboard of the magnets 42. Thus, as the magnets 42 on the implant move to the left or to the right, the magnets 46 on the prosthesis are maintained between the magnets 42 as they push the magnets 42 to the left or to the right, resulting in corresponding left and right movement of the prosthesis to simulate natural eye movement. The same magnetic coupling between the implant and the prosthesis can be achieved, using repelling forces, for up and down movement. For example, the prosthesis may be fitted with a single magnet 46 which is centered between four magnets 42 on the implant in an arrangement similar to that shown in FIG. 8. Similar to that described in connection with the embodiment of FIG. 7, the arrangement of four magnets 42 about a central magnet 46 will result in the central magnet 46 maintaining a centered position between the four magnets 42 on the implant when the poles are arranged to create repelling forces between the magnets 42 and the magnet 46.

Figure 11:
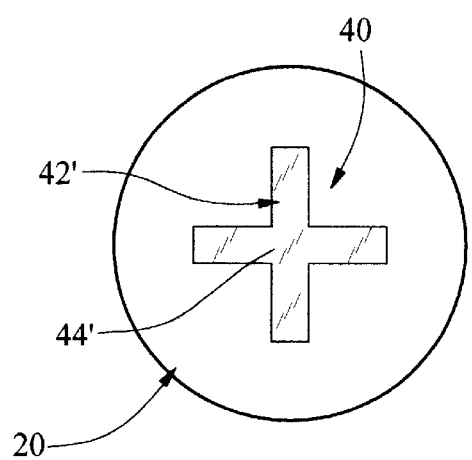
FIG. 11 is a front elevational view of the implant showing yet another embodiment of the magnet or magnetically attractive element, shown in the form of a cross having a horizontal component and a vertical component.

Referring to FIG. 11, an alternative embodiment of the invention is shown, wherein the magnet attracting metal element 42 is provided in the shape of a cross, including a horizontal component crossing with a vertical component. One or more magnets on the prosthesis are positioned to maintain a magnetic draw or force with the element 42'. The particular configuration of the metal element 42' promotes movement of the implant both in the up and down direction and laterally, from the medial side to the lateral excursion.

Figure 12:
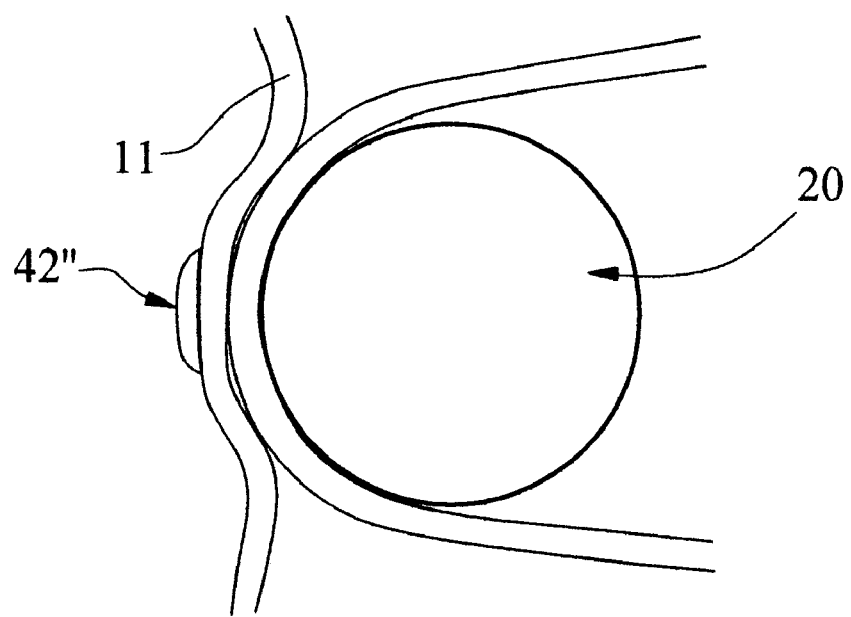
FIG. 12 is a side sectional anatomical view, illustrating a magnet or magnetically attractive metal element sutured to the exterior conjunctiva tissue in accordance with yet another embodiment of the present invention.
Figure 13:
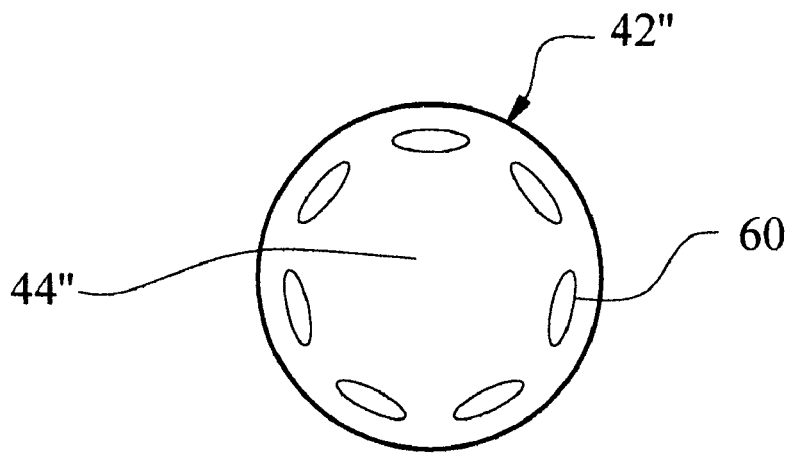
FIG. 13 is a front elevational view of the magnet or magnetically attractive element of the embodiment of FIG. 12.

Referring to FIGS. 12 and 13, yet another embodiment of the invention, wherein the metal element is provided in the form of a button or small plate 42" adapted to be surgically attached to the exterior conjunctiva tissue covering the implant 20. This particular embodiment is ideal for patients who have been previously fitted with integrated implants and do not want to have a hole drilled into the implant or undergo a surgical procedure to remove the implant or attachment of magnets or magnetically attracting elements thereto. To avoid potential complications associated with drilling a hole or further surgical procedures to remove the implant, the magnet attracting metal button 42", formed of a surgical metal material, is sutured to the exterior conjunctiva which covers the implant 20. The button 42" may be provided with apertures 60 about its periphery to facilitate suturing to the conjunctiva tissue. The button 42" is sutured with non-disintegrating sutures or staples and is specifically positioned to align with one or more magnets 46 fitted to the inner concave side of the prosthesis, in the manner described above. This particular system will also work with a non-direct alignment between the metal element button 42" and the magnets 46. In this instance, the metal element 42" and magnets are placed strategically so that when the metal element button 42" moves past the magnet(s) in prosthesis, natural eye movement of the prosthesis will result.

To replace a diseased or traumatized eye using the apparatus of the present invention, a surgical procedure is required wherein a standard enucleation is done, including tagging of the extraocular muscles with absorbable suture. The orbit is sized, using a set of sizing spheres, to determine the size of the implant to be used. An implant is of the proper size when it is the largest implant that can be placed deep into the orbit without creating tension on the overlying tissues and while allowing adequate room for an artificial eye of sufficient thickness. The implant may be placed into the orbit with or without being wrapped in a homologous or autologous material such as preserved sclera, dura or fascia lata. The surface of the hydroxyapatite material is very rough, and a wrapping material facilitates insertion and placement of the implant deep into the orbit. Additionally, a wrapped implant may be more resistance to exposure caused by abrasion from the surface of the implant on the overlying tissues. If some material is used to wrap the implant, the four rectus muscles should be sutured to the wrapping material.

The rectus muscles should be sutured to each other over the anterior aspect of the implant: lateral to medial and superior to inferior. Tenon's capsule and the conjunctiva should then be closed in separate layers. A temporary wrapping should be made to facilitate placement of the implant deep into the orbit. In one variation, the following technique can be used to place an unwrapped implant. Cut two 13×13 cm squares from the thin, sterile plastic drape used to drape the patient. Overlap two of the edges of the squares by about 1.0 cm and place the implant on the center of the overlap. Wrap the plastic around the implant and gather up the plastic to completely surround the implant. The plastic-wrapped implant can then be easily inserted into the orbit. After placing the implant deep into the orbit, unwrap the plastic and, while holding the implant in place with one finger, gently pull the plastic pieces out from under the implant. After a period of healing of approximately two months, the patient is measured for a cosmetic prosthesis. At this time, magnet positioning on the prosthesis can be determined for proper alignment of the prosthesis with the gaze position of the patient's natural eye, as described above.

In the instance an evisceration is preferable over enucleation, the medically accepted techniques for performing an evisceration are followed. The implant of the present apparatus is then inserted and the orbit is closed. The prosthesis is fitted in the same general manner as is done with the above enucleation procedure.

While the instant invention has been shown and described in what is considered to be preferred and practical embodiments thereof, it is recognized that departures from the instant disclosure are contemplated within the spirit and scope of the invention without limitation except as set forth in the following claims and under the doctrine of equivalents.

Now that the invention has been described,
What is claimed is:

1. An ocular replacement system for replacing a natural eye removed from an eye cavity having ocular tissue including muscle tissue and conjunctiva, said ocular replacement system comprising:
    a ball-shaped implant body sized and configured for receipt within the eye cavity and having an outer, generally spherical and porous surface that is receptive to ingrowth of the ocular tissue, and said surface including an anterior portion having a convex surface configuration defining a portion of said spherical surface, said anterior portion being structured and disposed to permit closing of the conjunctiva in covering relation to said anterior portion so that said implant body is completely enclosed within the eye cavity and covered by the ocular tissue;
    a prosthesis including an outer convex surface provided with a cosmetically acceptable appearance to resemble the natural eye and an inner concave surface;
    magnetic coupling means for coupling said prosthesis to said implant body through said ocular tissue covering said implant body so that said prosthesis follows movement of said implant body when said implant body moves within the eye cavity; and
    said magnetic coupling means including:
        at least one first magnet having an exposed face defining a magnetic pole, said at least one first magnet being imbedded within the anterior portion of said implant body so that said exposed face is flush with said outer, generally spherical and porous surface of said implant body on said anterior portion;
        at least one second magnet having an exposed face defining a magnetic pole, said at least one second magnet being fitted to said inner concave surface of said prosthesis so that said exposed face is flush with said inner concave surface of said prosthesis; and
        said at least one first magnet and said at least one second magnet being positioned and arranged relative to one another so that a magnetic force exists between said magnetic poles of said exposed faces of said at least one first magnet and said at least one second magnet.

2. An ocular replacement system as recited in claim 1 wherein said magnetic coupling means includes a plurality of said first magnets imbedded within the anterior portion of said implant body and including said exposed faces flush with said outer, generally spherical and porous surface of said anterior portion, and said exposed faces defining magnetic poles.

3. An ocular replacement system as recited in claim 1 wherein said magnetic coupling means includes a plurality of said second magnets each having said exposed face defining a magnetic pole, and said plurality of second magnets being fitted to said inner concave surface of said prosthesis so that said exposed faces are flush with said inner concave surface of said prosthesis.

4. An ocular replacement system as recited in claim 1 wherein said magnetic pole of said at least one first magnet and said magnetic pole of said at least one second magnet are of opposite polarity so that said magnetic force is an attracting force between said at least one first magnet and at least one second magnet.

5. An ocular replacement system as recited in claim 1 wherein said magnetic pole of said at least one first magnet and said magnetic pole of said at least one second magnet are of same polarity so that said magnetic force is a repelling force between said at least one first magnet and at least one second magnet.

6. An ocular replacement system for replacing a natural eye removed from an eye cavity having ocular tissue including muscle tissue and conjunctiva, said ocular replacement system comprising:
    a ball-shaped implant body sized and configured for receipt within the eye cavity and having an outer, generally spherical and porous surface that is receptive to ingrowth of the ocular tissue and including an anterior portion having a convex surface configuration defining a portion of said spherical surface of said implant body, said anterior portion being structured and disposed to permit closing of the conjunctiva in covering relation to said anterior portion so that said implant body is completely enclosed within the eye cavity and covered by the ocular tissue;
    a prosthesis including an outer convex surface provided with a cosmetically acceptable appearance to resemble the natural eye and an inner concave surface;
    magnetic coupling means for coupling said prosthesis to said implant body through said ocular tissue covering said implant body so that said prosthesis follows movement of said implant body when said implant body moves within the eye cavity; and
    said magnetic coupling means including:
        at least one first magnet having an exposed face defining a magnetic pole, said at least one first magnet being imbedded within the anterior portion of said implant body so that said exposed face is flush with said outer, generally spherical and porous surface of said implant body on said anterior portion;
        at least one second magnet having an exposed face defining a magnetic pole, said at least one second magnet being fitted to said inner concave surface of said prosthesis so that said exposed face is flush with said inner concave surface of said prosthesis; and
        said magnetic pole of said at least one first magnet and said magnetic pole of said at least one second magnet being of the same polarity and said at least one first magnet and said at least one second magnet being positioned and arranged relative to one another so that a repelling magnetic force exists between said magnetic poles of said exposed faces of said at least one first magnet and said at least one second magnet.

7. An ocular replacement system as recited in claim 6 wherein said magnetic coupling means includes a plurality of said first magnets imbedded within the anterior portion of said implant body and including said exposed faces flush with said outer, generally spherical and porous surface of said anterior portion, and said exposed faces defining magnetic poles.

8. An ocular replacement system as recited in claim 6 wherein said magnetic coupling means includes a plurality of said second magnets each having said exposed face defining a magnetic pole, and said plurality of second magnets being fitted to said inner concave surface of said prosthesis so that said exposed faces are flush with said inner concave surface of said prosthesis.

9. An ocular replacement system for replacing a natural eye removed from an eye cavity having ocular tissue including muscle tissue and conjunctiva, said ocular replacement system comprising:
    a ball-shaped implant body sized and configured for receipt within the eye cavity and having an outer, generally spherical and porous surface that is receptive to ingrowth of the ocular tissue and including an anterior portion having a convex surface configuration defining a portion of said spherical surface of said implant body, said anterior portion being structured and disposed to permit closing of the conjunctiva in covering relation to said anterior portion so that said implant body is completely enclosed within the eye cavity and covered by the ocular tissue;

a prosthesis including an outer convex surface provided with a cosmetically acceptable appearance to resemble the natural eye and an inner concave surface;

magnetic coupling means for coupling said prosthesis to said implant body through said ocular tissue covering said implant body so that said prosthesis follows movement of said implant body when said implant body moves within the eye cavity; and said magnetic coupling means including:
  at least one first magnet having an exposed face defining a magnetic pole, said at least one first magnet being imbedded within the anterior portion of said implant body so that said exposed face is flush with said outer, generally spherical and porous surface of said implant body on said anterior portion;
  at least one second magnet having an exposed face defining a magnetic pole, said at least one second magnet being fitted to said inner concave surface of said prosthesis so that said exposed face is flush with said inner concave surface of said prosthesis; and
  said magnetic pole of said at least one first magnet and said magnetic pole of said at least one second magnet being of opposite polarity and said at least one first magnet and said at least one second magnet being positioned and arranged relative to one another so that an attracting magnetic force exists between said magnetic poles of said exposed faces of said at least one first magnet and said at least one second magnet.

10. An ocular replacement system as recited in claim 9 wherein said magnetic coupling means includes a plurality of said first magnets imbedded within the anterior portion of said implant body and including said exposed faces flush with said outer, generally spherical and porous surface of said anterior portion, and said exposed faces defining magnetic poles.

11. An ocular replacement system as recited in claim 9 wherein said magnetic coupling means includes a plurality of said second magnets each having said exposed face defining a magnetic pole, and said plurality of second magnets being fitted to said inner concave surface of said prosthesis so that said exposed faces are flush with said inner concave surface of said prosthesis.

* * * * *